United States Patent
Mata

(10) Patent No.: US 7,820,147 B2
(45) Date of Patent: Oct. 26, 2010

(54) HAIR RESTORATIVE COMPOSITIONS AND METHODS FOR TREATING DAMAGED HAIR AND SAFELY CHEMICALLY TREATING HAIR

(76) Inventor: Michael T. Mata, 8642 Timber Lodge, San Antonio, TX (US) 78250

( * ) Notice: Subject to any disclaimer, the term of this patent is extended or adjusted under 35 U.S.C. 154(b) by 1173 days.

(21) Appl. No.: 11/282,892

(22) Filed: Nov. 18, 2005

(65) Prior Publication Data

US 2007/0116661 A1    May 24, 2007

(51) Int. Cl.
A61K 8/18      (2006.01)
A61K 8/72      (2006.01)
A61Q 5/12      (2006.01)
A61Q 5/06      (2006.01)

(52) U.S. Cl. ............. 424/70.1; 424/70.11; 424/70.122; 424/70.16

(58) Field of Classification Search ................ 424/70.1, 424/70.11, 70.122, 70.16
See application file for complete search history.

(56) References Cited

U.S. PATENT DOCUMENTS

| | | | |
|---|---|---|---|
| 3,954,113 A | 5/1976 | Bohrer et al. | |
| 4,156,067 A | 5/1979 | Gould | 424/78.06 |
| 4,172,887 A | 10/1979 | Vanlerberghe et al. | 424/70.17 |
| 4,638,822 A | 1/1987 | Grollier et al. | 132/209 |
| 4,871,530 A | 10/1989 | Grollier et al. | 424/47 |
| 5,139,037 A | 8/1992 | Grollier et al. | 132/203 |
| 5,294,437 A * | 3/1994 | Shah et al. | 424/70.12 |
| 5,635,168 A | 6/1997 | Burns et al. | 424/70.4 |
| 5,653,963 A | 8/1997 | Beitone et al. | 424/47 |
| 5,660,820 A | 8/1997 | Mondet et al. | 424/70.16 |
| 5,709,850 A | 1/1998 | Mondet et al. | 424/70.16 |
| 5,726,137 A | 3/1998 | Patel et al. | 510/122 |
| 5,753,216 A | 5/1998 | Leitch et al. | 424/70.12 |
| 5,830,440 A | 11/1998 | Sturla et al. | 424/47 |
| 6,048,520 A | 4/2000 | Hoshowski | 424/70.17 |
| 6,125,856 A | 10/2000 | Yamashita | 132/204 |
| 6,153,208 A | 11/2000 | McAtee et al. | 424/402 |
| 6,156,295 A | 12/2000 | Shah | |
| 6,162,423 A | 12/2000 | Sebag et al. | 424/70.12 |
| 6,338,855 B1 | 1/2002 | Albacarys et al. | 424/409 |
| 6,383,995 B1 | 5/2002 | Maurin et al. | 510/119 |
| 6,383,996 B1 | 5/2002 | Maurin et al. | 510/119 |
| 6,403,073 B1 | 6/2002 | Cauwet-Martin et al. | 424/70.1 |
| 6,432,420 B2 | 8/2002 | Ellis et al. | 424/401 |
| 6,432,894 B1 | 8/2002 | Maurin et al. | 510/122 |
| 6,471,952 B1 | 10/2002 | Dubief et al. | 424/70.12 |
| 6,482,808 B1 | 11/2002 | Springob et al. | 514/99 |
| 6,511,671 B1 | 1/2003 | Dubief et al. | 424/401 |
| 6,534,455 B1 | 3/2003 | Maurin et al. | 510/124 |
| 6,544,499 B1 | 4/2003 | Glenn, Jr. et al. | 424/70.1 |
| 6,562,772 B1 | 5/2003 | Maurin et al. | 510/124 |
| 6,645,478 B2 | 11/2003 | Rollat et al. | 424/70.1 |
| 6,667,378 B2 | 12/2003 | Rollat et al. | 526/266 |
| 6,689,346 B1 | 2/2004 | Rollat et al. | 424/70.1 |
| 2001/0008631 A1 | 7/2001 | Ellis et al. | 424/400 |
| 2002/0179108 A1 | 12/2002 | Harrison | 132/201 |
| 2004/0258652 A1 | 12/2004 | Pascaly et al. | 424/70.27 |
| 2005/0019289 A1 | 1/2005 | Hirata et al. | 424/70.1 |
| 2005/0048021 A1 | 3/2005 | Salem et al. | 424/70.14 |
| 2005/0089494 A1 | 4/2005 | Rigoletto, Jr. | 424/70.15 |
| 2005/0226838 A1 | 10/2005 | Krause et al. | 424/70.13 |
| 2005/0232893 A1 | 10/2005 | Kaharu et al. | 424/70.27 |

OTHER PUBLICATIONS

Berge et al. (Journal of Pharmaceutical Sciences, vol. 66, No. 1, pp. 1-19; 1977).*

* cited by examiner

*Primary Examiner*—Raymond J Henley, III
(74) *Attorney, Agent, or Firm*—Workman Nydegger

(57) ABSTRACT

Hair restorative compositions useful in repairing damaged hair include at least one hair shaft bonding agent dispersed within an appropriate solvent or carrier, such as water. When applied to damaged hair, the hair shaft bonding agent adsorbs into and bonds to the damaged hair shaft, filling in discontinuities and adhering split ends or loosened cuticle layers back together within the main hair shaft. A wetting agent may be included to facilitate absorption and bonding of the hair shaft bonding agent to hair. A thickening agent may be included to yield a hair restorative composition that is much easier to apply compared to runny compositions having the consistency of water. A conditioner may be added to nourish and condition the hair. The inventive hair restorative compositions are able to permanently repair damaged hair, thereby resulting in hair that is stronger, healthier, and more resistant to further damage.

25 Claims, No Drawings

HAIR RESTORATIVE COMPOSITIONS AND METHODS FOR TREATING DAMAGED HAIR AND SAFELY CHEMICALLY TREATING HAIR

CROSS-REFERENCE TO RELATED APPLICATIONS

[None]

BACKGROUND OF THE INVENTION

1. The Field of the Invention

The present invention is in the field of hair care products, more particularly hair restorative compositions and methods for treating (e.g., strengthening) damaged hair.

2. The Relevant Technology

In today's glamour-conscious society, a person's appearance can determine many things, including social status and economic success. Looking one's best is often a top priority. Many beautifying treatments have been developed, and continue to be developed, which are designed to help people change the appearance of their hair. These include hair color or bleaching treatments for people who want a different color hair, permanents and body waves for people with straight or flat hair, hair relaxation treatments for people with wavy or kinky hair, each of which alters the chemical structure of hair in some way. In general, the more radical the change in hair appearance, the greater will be the chemical alteration of, and potential damage to, the hair.

The unfortunate byproduct of the many hair treatments is that chemically treated hair can easily become damaged. Natural forces such as salt water and sunlight are also known to damage hair. Damaged hair is characterized by unnatural discontinuities in the protein structure of the individual hair strands or shafts. Examples include split ends, dry straw-like hair, hair that is easily broken, and hair that is generally frizzed-out and unmanageable. Because the visible portion of hair is dead, it has no ability to regenerate itself. The only way to naturally regenerate one's hair is to allow healthy hair to grow out and replace the damaged portion.

Because hair is dead and lacks regenerative properties, the end result of over-treating hair can be worse than not treating hair at all. Because of this, persons who never treat their hair generally have healthier hair over the long run than people who treat their hair. Therefore, while spending a lot of money on expensive hair beautification treatments can yield desirable short-term results, the long-term result is often hair that is damaged and even less attractive than before such treatments were performed. This can pose a Faustian dilemma, particularly to people who are required by their profession to have treated hair, such as models and actors.

There are numerous over-the-counter and salon treatments that purport to fix damaged hair. These include conditioners, hot oil treatments, hydrolyzed proteins, vitamin formulations, and exotic fruit, leaf or root extracts that are said to be absorbed by the hair. In reality, such treatments only coat the hair shafts superficially with foreign materials that do not become permanently integrated within the protein structure of the hair. In the short run, coating dry, damaged or split hair with certain materials can cause the hair to look better. However, such materials generally wash off each time the hair is shampooed, requiring continued application to obtain any long-term benefit. Materials that do not wash off easily can build up over time, requiring periodic deep cleansing treatments to remedy that problem. The end result is that such treatments can mask but not reverse the underlying damage to the protein structure associated with physically or chemically damaged hair.

In the end, the objective consensus of experts who study hair is that none of the many highly touted conditioners, hot oil treatments, protein, vitamin or natural product treatments actually remedies the underlying damage to the protein structure of hair. Such treatments are in most cases completely worthless if the goal is to permanently reverse hair damage. In a common scenario, a person shampoos his or her hair, which strips the hair of natural oils secreted by the scalp, which are intended to naturally moisturize the otherwise dry, dead protein structure of a person's hair. Thereafter, the person applies a conditioner to restore or replace the stripped oils, usually with an oil, fatty acid, protein, carbohydrate, or humectant that is actually foreign to the hair. Though this cycle is, at some level, self-defeating and pointless, it is typically repeated on a daily basis. For a more long-term solution, hair salons and professional hair stylists offer special conditioning treatments, usually at much greater expense. In short, the consensus among hair experts is that once hair has been damaged, it will remain damaged until new hair grows out to take its place.

This can, and often does, have devastating consequences on persons who make a living looking beautiful, especially models. One model was told, after her hair was severely damaged, that she would have to retire for seven months until new hair could grow in to replace the damaged hair. In more general terms, people would simply like to have the option of having their hair treated without the risk of irreparably damaging their hair.

In view of the foregoing, there is a tremendous need, long felt in the art, to provide improved remedies or treatments that can reverse the effects of physical and chemical damage to hair.

BRIEF SUMMARY OF THE PREFERRED EMBODIMENTS

The present invention generally relates to hair restorative compositions and methods for repairing damaged hair. The inventive hair restorative compositions include ingredients that are able to chemically bond to hair in order to fill in and permanently mend discontinuities in the protein structure of damaged hair. The result is more continuous hair strands that appear healthier and more natural than damaged hair. In many cases, badly damaged hair can be restored to a stronger, healthier appearance after just one treatment. In addition, the hair restorative compositions permit multiple hair treatments involving harsh chemicals (e.g., coloring, curling, straightening, etc.) in a single visit. Treating hair with the inventive hair restorative compositions allows one to safely chemically treat hair without causing severe permanent damage to the hair structure.

The inventive hair restorative compositions include one or more hair shaft bonding agents that are able to chemically react with and bond to hair. In a preferred embodiment, the hair shaft bonding agent is included in an amount greater than 5% by weight of the hair restorative composition. By way of example, the hair shaft bonding agent may include at least one adhesive or bonding agent based on acrylic acid or methacrylic acid (e.g., Luvimer 100P sold by BASF).

One or more wetting agents are preferably included to improve the ability of the hair shaft bonding agent to absorb into and bond with damaged hair shafts. By way of example, the wetting agent may include dimethicone copolyol (e.g., DC 190 sold by Dow Corning). Although Luvimer 100P is able to adhere to hair, the ability of Luvimer 100P to absorb or penetrate into the hair during the treatment process can be improved by adding Si-Tec DMC.

Although the precise mechanism by which the inventive hair restorative compositions are able to repair damaged hair is not completely understood, it is currently believed that the hair shaft bonding agent adheres to damage hair shafts, fills in any discontinuities, and rejoins any split or frayed portions with the main hair shaft. Thus, places where the hair shaft cuticle has been partially detached or removed completely are filled in. Split ends are fused back together. The result is a more uniform hair shaft surface, which strengthens the cuticle of the hair shaft, protects the softer underlying layers of protein, and results in hair shafts that are stronger, more manageable, and able to undergo further hair treatments. This repair process is improved when a wetting agent is used in combination with the hair shaft bonding agent.

In one embodiment, one or more thickening agents are added in order to alter the rheology or consistency of the composition so that it can be applied more evenly, while reducing or eliminating waste. An example of a useful thickening agent is hydroxyethyl cellulose (e.g., Cellosize PCG-10, sold by The Dow Chemical Company). The thickening agent increases the viscosity of the composition and results in a composition having the consistency of a cream or lotion that more easily stays where placed. In the absence of a thickening agent, the hair restorative composition is more fluid, having a consistency more like water, which can make it difficult to apply in even amounts throughout the damaged hair without requiring a large excess. Applying a large excess of restorative composition is not only wasteful but can be uncomfortable and messy, particularly as the composition begins to stiffen or solidify during the hair restoration process.

In another embodiment, one or more softening agents are added to the hair restorative compositions in order to alter the degree or manner in which the hair bonding agent solidifies. The softening agent can result in a hair restorative composition that is less hard and/or less sticky when used to treat damaged hair compared to a hair restorative composition in the absence of a softening agent. Hair restorative compositions that do not include any softening agent can become quite sticky as they react with hair and, ultimately, quite rigid upon completion of the hair restorative procedure. Such compositions typically require the treated hair to be washed multiple times to finally remove the solidified hair restorative composition. In contrast, including a softening agent can result in a final reacted composition that is more easily washed off. In some cases, it can be removed in a single washing. In some cases, the wetting agent discussed above can also serve as a softening agent.

In yet another embodiment, one or more proteins may be added to the hair restorative compositions in order to help nourish and condition the treated hair. An example of a suitable protein-based conditioner is hydrolyzed wheat protein (e.g., Wheat Pro EN-20, sold by Arch Chemicals, Inc.). Whereas proteins or amino acids will not themselves permanently bond to hair, proteins or amino acids contained in formulations that include a hair shaft bonding agent can, in fact, become attached to the protein structure of a hair shaft. The result is hair that is stronger, shinier, and less brittle compared to hair that is repaired in the absence of a protein additive.

Hair restorative compositions according to the invention may also include other ingredients or adjuvents as desired in order to yield a hair restorative composition having desired properties. Examples of other ingredients or adjuvents include, but are not limited to, solvents for dissolving, suspending, or diluting any of the active ingredients (e.g., water), pH adjusters or buffers (e.g., aminomethyl propanol), humectants, emulsifying agents, oils, preservatives (e.g., Germaben II E, sold by ISP Corp.), fragrances, and the like.

The hair restorative compositions according to the invention can be formulated so as to be a dedicated hair restorative treatment. Alternatively, they can be added to existing hair care products, such as shampoos, coloring and bleaching treatments, permanent treatments, hair relaxation treatments, conditioners, hair tonics, styling gels, hair sprays, creams, lotions, and the like. They can be formulated so as to be an additive that a user can add to his or her favorite hair products. When used in connection with a coloring treatment, the hair shaft bonding agent also helps to encapsulate the dyes or pigments within the hair shafts. The result is hair that maintains its new color significantly longer (e.g., up to 6 months longer).

In use, the inventive hair restorative compositions are applied to a person's hair and left in place for a time sufficient to at least partially bond to and restore damaged hair. To facilitate hardening or curing of the hair shaft bonding agent, the hair restorative composition can be dried using heated air (e.g., by means of a blow dryer, preferably without combing). Thereafter, the hardened composition is typically washed out of the hair in order to remove excess hair repair composition. In the case of styling gels, hair sprays, tonics and the like, excess hair restorative composition may be washed out later.

The hair restorative compositions can be used in connection with a variety of chemical hair treatments well known in the art, including but not limited to, hair straightening, perming, body waving, bleaching, coloring and highlighting. According to a presently preferred embodiment, it is advantageous to first treat the hair with a hair restorative composition according to the invention and then chemically treat the hair according to known methods. Treating the hair first with the hair restorative composition creates greatly strengthened hair that can better accept and not be damaged by harsh chemicals within the chemical treatments. In general, the hair is advantageously pretreated with the inventive hair restorative composition before each chemical treatment.

These and other advantages and features of the present invention will become more fully apparent from the following description and appended claims, or may be learned by the practice of the invention as set forth hereinafter.

DETAILED DESCRIPTION OF THE PREFERRED EMBODIMENTS

The present invention generally relates to hair restorative compositions used to repair damaged hair, and methods for using such composition. The inventive hair restorative compositions include ingredients that chemically bond to damaged hair and fill in discontinuities in the protein structure of damaged hair shafts. The hair restorative compositions permit multiple hair treatments involving harsh chemicals (e.g., coloring, curling, straightening, etc.) in a single visit. Treating hair with the inventive hair restorative compositions is the only way to safely chemically treat hair without causing severe damage to the hair structure.

The hair restorative compositions according to the invention include one or more hair shaft bonding agents dispersed within an appropriate solvent or carrier. In one embodiment, the solvent or carrier comprises water (e.g., water filtered by reverse osmosis). When the hair shaft bonding agent is placed in contact with damaged hair, it first absorbs into the hair shafts and then bonds to the hair as it cures or solidifies.

Evaporation of the water or other solvent facilitates hardening or curing of the hair shaft bonding agent.

Damaged hair shafts are characterized by damage to the cuticle, or hard outer protective layer of the hair shaft. The cuticle normally overlaps in layers to protect the underlying softer protein structure. When the outer cuticle layer(s) of a hair shaft becomes damaged, the soft underlying protein structure is exposed to chemical or physical damage. Loss of the cuticle layer also allows the underlying layers to lose structure and form ridges, fissures and nodules. The hair shaft bonding agent repairs damaged hair shafts by adhering back together any loosened cuticle layers, rejoining split ends, and filling in gaps where the cuticle layer has been removed completely.

Examples of hair shaft bonding agents within the scope of the invention include adhesives based on at least one of acrylic acid or methacrylic acid. More specific examples of hair shaft bonding agents include, but are not limited to, acrylic acids, acrylic acid oligomers, acrylic acid polymers, acrylic acid copolymers, acrylates, acrylate oligomers, acrylate polymers, acrylate copolymers, methacrylic acids, methacrylic acid oligomers, methacrylic acid polymers, methacrylic acid copolymers methacrylates, methacrylate oligomers, methacrylate polymers, and methacrylate copolymers.

In one currently preferred embodiment, the hair shaft bonding agent comprises a mixture of t-butyl acrylate, methacrylic acid, and ethylacrylate copolymer. An example of a hair shaft bonding agent comprising the foregoing components is Luvimer 100P, which is available from BASF.

The hair shaft bonding agent may be included in an amount that yields a hair restorative composition capable of restoring hair. The concentration of the hair shaft bonding agent will vary depending on the identities and concentrations of the other ingredients within the hair restorative composition. Hair restorative composition may include the one or more hair shaft bonding agents in an amount in a broad range of about 1% to about 50% by weight of the hair restorative composition. However, superior results are obtained when the hair shaft bonding agent is included in an amount greater than 5% by weight, e.g., in a range of about 5.5% to about 30% by weight of the hair restorative composition, more preferably in a range of about 6% to about 25% by weight of the hair restorative composition, and most preferably in a range of about 7% to about 20% by weight of the hair restorative composition.

The inventive hair restorative compositions according to the invention may also include one or more wetting agents that improve the ability of the hair shaft bonding agent to absorb into and bond with the damaged hair shafts that are being repaired. According to one currently preferred embodiment, the wetting agent includes dimethicone copolyol, an example of which is DC 190, which is available from Dow Corning. Another example is Si-Tec DMC, which is available from ISP Corp. Other wetting agents may also be used as desired, examples of which include other silicone polymers. Although hair shaft bonding agents are able to adhere to hair in the absence of a wetting agent, their ability to absorb or penetrate into the hair during a hair reparation process can be greatly improved by adding one or more wetting agents, such as a dimethicone copolyol.

The wetting agent may be included in any desired amount in order to yield a hair restorative composition having desired hair restorative and other properties. The concentration of the wetting agent will vary depending on the identities and concentrations of the other ingredients within the hair restorative composition. When a wetting agent is included, hair restorative compositions according to the invention preferably include the one or more wetting agents in an amount in a range of about 0.01% to about 10% by weight of the hair restorative composition, more preferably in a range of about 0.1% to about 5% by weight of the hair restorative composition, and most preferably in a range of about 0.2% to about 1% by weight of the hair restorative composition.

One or more thickening agents may be added in order to alter the rheology or consistency of the composition so that it can be applied more evenly, while reducing or eliminating waste. The thickening agent increases the viscosity of the composition and results in a composition having the consistency of a cream or lotion that more easily stays where placed. In the absence of a thickening agent, the hair restorative composition is more fluid, having a consistency more like water, which can make it difficult to apply evenly throughout the damaged hair without requiring a large excess. Applying a large excess of particularly as the composition begins to stiffen or solidify during the hair restoration process.

Examples of useful thickening agents include, but are not limited to, any of the various cellulosic ethers known in the art. A currently preferred thickening agent includes hydroxyethyl cellulose, an example of which is Cellosize PCG-10, which is sold by The Dow Corporation. Another example is hydroxyethyl cellulose sodium acetate, such as Cellosize 52000H also sold by The Dow Corporation. Other useful thickening agents include, but are not limited to, carboxypolymethylene, polyethylene oxide, polyacrylic acids, copolymers of polyacrylic acid, polyacrylates, polyacrylamides, copolymers of polyacrylic acid and polyacrylamide, polyvinylpyrrolidone (PVP), PVP-vinyl acetate copolymers, carboxymethylcellulose, carboxypropylcellulose, polysaccharide gums, and proteins.

The thickening agent may be included in any desired amount in order to yield a hair restorative composition having desired hair restorative and other properties. The concentration of the thickening agent will vary depending on the identities and concentrations of the other ingredients within the hair restorative composition. When a thickening agent is included, hair restorative compositions according to the invention preferably include the one or more thickening agents in an amount in a range of about 0.01% to about 10% by weight of the hair restorative composition, more preferably in a range of about 0.1% to about 5% by weight of the hair restorative composition, and most preferably in a range of about 0.2% to about 1% by weight of the hair restorative composition.

One or more softening or plasticizing agents may be added to the hair restorative compositions in order to alter the degree or manner in which the hair shaft bonding agent solidifies. Softening or plasticizing agents can result in a hair restorative composition that is less hard and/or less sticky when used to treat damaged hair compared to a hair restorative composition in the absence of a softening agent. Compositions without a softening or plasticizing agent typically require the treated hair to be washed multiple times to finally remove the solidified hair restorative composition. In contrast, including a softening or plasticizing agent can result in a final reacted composition that is more easily washed off. In some cases, it can be removed in a single washing.

It has been found that when dimethicone copolyol is used as the wetting agent, it can also serve as a softening or plasticizing agent for the hair restorative composition, more particularly the hair shaft bonding agent. It is also within the scope of the invention to include other softening or plasticizing agents known in the art to yield hair restorative compositions that do not overly embrittle during hair reparation treatments and which are more easily washed out of the hair upon completion of the hair reparation treatments.

One or more conditioners may also be added to nourish and condition the hair during the hair reparation process. In one embodiment, proteins or amino acids may be added to the hair restorative compositions as a conditioner. One currently preferred protein-based conditioner is hydrolyzed wheat protein, an example of which is Wheat Pro EN-20, sold by Arch Chemicals, Inc. Another example of hydrolyzed wheat protein is Conditioneze HW, available from ISP Corp. Whereas proteins or amino acids will not themselves permanently bond to hair, proteins or amino acids contained in formulations that include a hair shaft bonding agent can, in fact, become incorporated into the protein structure of the hair shaft. The result is hair that is stronger, shinier, and less brittle compared to hair that is repaired in the absence of a conditioner.

Hair restorative compositions according to the invention may also include a pH adjuster or buffer to yield a composition having a desired pH or pH range. In the case were acidic ingredients are used (e.g., methacrylic acid), it may be desirable to add a base in order to raise the pH. Examples of suitable pH adjusters include metal oxides and hydroxides, ammonium hydroxide, and alkyl amines. One currently preferred alkyl amine pH adjuster is aminomethyl propanol, an example of which is AMP-95, sold by The Dow Chemical Company.

Hair restorative compositions according to the invention may also include humectants, emulsifying agents, oils, preservatives, fragrances, and the like. Preservatives and germicides may be used in order to prevent spoilage, particularly where natural ingredients that can provide a food source for bacteria are included (e.g., hydrolyzed wheat protein). Preservatives according to the invention include, but are not limited to, methylparaben and propylparaben. A currently preferred preservative is Germaben II E, which is a mixture of propylene glycol, diazolidinyl urea, methylparaben and propylparaben available from ISP Corp.

The hair restorative compositions according to the invention can be formulated so as to be a dedicated hair restorative treatment. Alternatively, they can be added to existing hair care products, such as shampoos, coloring and bleaching treatments, permanent treatments, hair relaxation treatments, conditioners, hair tonics, styling gels, hair sprays, creams, lotions, and the like. They can be formulated so as to be an additive that a user can add to his or her favorite hair products.

It has been discovered that when hair restorative compositions according to the invention are used in connection with a coloring treatment, the hair shaft bonding agent also helps to encapsulate the dyes or pigments within the hair shafts. The result is hair that maintains its new color significantly longer (e.g., up to 6 months longer). In one embodiment, a hair restorative composition according to the invention is added to or comprises a conditioning treatment that is applied immediately the hair is colored or dyed.

In use, the inventive hair restorative compositions are applied to a person's hair and left in place for a time sufficient to at least partially bond to and restore damaged hair. To facilitate hardening or curing of the hair shaft bonding agent, the hair restorative composition can be dried using heated air (e.g., by means of a blow dryer, preferably without combing). Thereafter, the hardened composition is typically washed out of the hair in order to remove excess hair repair composition. In the case of styling gels, hair sprays, tonics and the like, excess hair restorative composition may be washed out later.

The hair restorative compositions can be used in connection with a variety of chemical hair treatments well known in the art, including but not limited to, hair straightening, perming, body waving, bleaching, coloring and highlighting. According to a presently preferred embodiment, it is advantageous to first treat the hair with a hair restorative composition according to the invention and then chemically treat the hair according to methods that are known to those of skill in the art. Treating the hair first with the hair restorative composition creates greatly strengthened hair that can better accept and not be damaged by harsh chemicals within the chemical treatments. In general, the hair is advantageously pretreated with the inventive hair restorative composition before each chemical treatment. For example, if two chemical treatments are to be performed, it is advantageous to pretreat the hair with a hair treatment composition according to the invention before the first chemical treatment and then pretreat the hair again with the hair treatment composition before performing the second chemical treatment.

EXAMPLES OF THE PREFERRED EMBODIMENTS

The following are several examples of hair restorative compositions that have been formulated and manufactured according to the invention. The exemplary formulations and manufacturing conditions are given by way of example, and not by limitation, in order to illustrate hair restorative compositions that have been found to be useful repairing damaged hair. Unless otherwise indicated, all percentages are by weight.

Example 1

An improved hair restorative composition suitable for repairing damaged hair was prepared by combining the following components in the amounts listed below:

| | |
|---|---|
| Deionized water | 86.25 parts |
| Luvimer 100P | 10.0 parts |
| Hydrolized wheat protein | 0.75 part |
| Hydroxyethyl cellulose | 0.5 part |
| Aminomethyl propanol | 1.0 part |
| Dimethicone copolyol | 0.5 part |
| Germaben II | 0.5 part |
| Fragrance | 0.5 part |

Luvimer 100P is an adhesive composition sold by BASF containing a proprietary blend of t-butyl acrylate, methacrylic acid, and ethylacrylate copolymer. Germaben II is a germicidal composition sold by ISP Corp. containing a proprietary blend of propylene glycol, diazolidinyl urea, methylparaben, and propylparaben.

The hair restorative composition of this example was made as follows. In a tank equipped with sweep agitation and containing a portion (36.25 parts out of 86.25) of the water, the hydroxyethyl cellulose (Cellosize PCG-10) was sifted into the water. A portion of the water was recirculated through the valve to prevent caking. The mixture was mixed for approximately 1 hour after which a portion (0.10 out of 1.00 part) the aminomethyl propanol (AMP-95) was added while continuing to mix to form Phase A.

In a separate vessel equipped with rapid agitation and containing the remainder (i.e., 50.00 parts out of 86.25) of the water, the remaining portion of the AMP-95 (i.e., 0.90 part out of 1.00 part) was added to the vortex of the water. Thereafter, the Luvimer 100P was sifted into the vorex of the water/AMP-95 mixture to form Phase B.

After Phase A was thickened and Phase B became clear, Phase B was slowly added to the vessel containing phase A by pumping bottom to bottom.

After mixing together Phase A and Phase B, the hydrolyzed wheat protein (Wheat Pro EN-200), Germaben II E, fragrance, and dimethicone copolyol (DC 190 Fluid) were added while continuing to stir for 1 to 2 hours. The hair restorative composition had the consistency of a cream or lotion.

The hair restorative composition was applied and worked into damaged hair. The thickening agent (Cellosize PCG-10) imparted a rheology to the hair restorative composition that facilitated application of the composition to a person's hair. The composition could be placed into the palm of a hand or applied directly to a person's head without the composition running through a person's fingers or running off a person's head, which occurred in compositions without a thickening agent. While compositions that lack a thickening agent will also restore hair, they are more difficult to apply and result in more waste. The thickened composition more reliably stayed where placed, which facilitated the ability to work the composition around to coat all the person's hair. Thereafter, the composition was allowed to dry (e.g., by means of a blow dryer).

The dimethicone copolyol facilitating wetting of the Luvimer 100P to the hair, which allowed it to better absorb into and adhere to the hair compared to hair restorative compositions that do not include a wetting agent. It is believed that dimethicone copolyol also acted to plasticize the hair restorative composition as it cured or hardened during the hair reparation process. When left onto the hair until dry, hair restorative compositions that included dimethicone copolyol were less rigid, preventing or reducing the effect of what was euphemistically called "helmet hair", which resulted when a composition lacking a plasticizing or softening agent was allowed to harden on a person's head during a hair restoration treatment.

The hydrolyzed wheat protein was added as a conditioner, and was believed to penetrate into and be absorbed by the hair. The wheat protein was added to nourish the hair, and was believed to have been encapsulated within the hair by the Luvimer 100P. In this way, it was not easily washed out of the hair subsequently, as occurs when using ordinary protein-based conditioners.

The hair restorative composition succeeded in repairing damaged hair, even very badly damaged hair. In some cases, the repaired hair appeared to be very shiny and strong, like normal hair that is not damaged. The repaired hair reflected light, whereas the damaged hair scattered light, thus creating an improved cosmetic look in addition to strengthening the hair by filling in discontinuities in the cuticles of the hair shafts.

The hair restorative composition allowed for body waving, perming, straightening, bleaching, and/or coloring all in the same day without unduly damaging the person's hair.

Example 2

An alternative hair restorative composition was prepared by combining the following components in the concentrations listed below:

| Deionized water | 91.75% |
| --- | --- |
| Luvimer 100P | 5.0% |
| Hydrolized wheat protein | 0.75% |
| Hydroxyethyel cellulose sodium acetate | 0.5% |
| Aminomethyl propanol | 0.5% |
| Dimethicone copolyol | 0.5% |
| Germaben II | 0.5% |
| Fragrance | 0.5% |

The hair restorative composition was made as follows. Hydroxyethyl cellulose sodium acetate (Cellosize HEC QP 52000H) was added to water that was heated sufficiently to dissolve the hydroxyethyel cellulose sodium acetate. The mixture was mixed for 15 minutes until clear. Thereafter, aminomethyl propanol was added while continuing to mix. Dimethicone copolyol (Si-Tec DMC) was added while continuing to mix. Wheat protein (Conditioneze HW) was then added while continuing to mix. Thereafter, Luvimer 100P was added and the resulting mixture was mixed for 30 minutes. Germaben II was added while continuing to mix. Fragrance was added while continuing to mix to yield the final hair restorative composition. The hair restorative composition had the consistency of a cream or lotion.

While the hair restorative composition of Example 2 possessed many of the advantages of the hair restorative composition of Example 1, the composition of Example 2 was not as effective in repairing damaged hair as the composition of Example 1. The composition of Example 1 was far more effective in repairing damaged hair compared to the composition of Example 2.

Example 3

The hair restorative composition of Example 1 or 2 is modified by omitting the thickening agent. The modified hair restorative composition of Example 3 is much more runny than the composition of Examples 1 or 2 and is, therefore, more difficult to apply to damaged hair. When applied to a person's hand or head, the composition of Example 3 more easily runs or drips off. Nevertheless, the hair restorative composition of Example 3 works in restoring hair. Moreover, this composition can be added to an existing hair treatment composition, such as a rinse or conditioner that contains a thickening agent.

Example 4

The hair restorative composition of Examples 1 or 2 is modified by omitting the demethicone copolyol. The hair shaft bonding agent (Luvimer 100P) is able to bond to hair, but without a wetting agent, it takes longer for the Luvimer 100P to penetrate into and bond to the hair. The composition is harder to wash out of a person's hair upon completing the restoration process. Nevertheless, the hair restorative composition of Example 4 works in restoring hair. Moreover, this composition can be added to an existing hair treatment composition, such as a rinse or conditioner that contains a wetting agent.

Example 5

The hair restorative composition of Examples 1 or 2 is modified by omitting the hydrolyzed wheat protein. The modified hair restorative composition of Example 5 is easy to apply and the hair shaft bonding agent (Luvimer 100P) is able to readily absorb into and bond to hair. The composition is easy to wash out of a person's hair upon completing the restoration process. However, without a conditioner, the treated hair is not as nourished and healthy as hair that includes hydrolyzed wheat protein. Nevertheless, the hair restorative composition of Example 5 works in restoring hair.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of strengthening damaged or chemically treated hair, comprising:
    (a) applying to damaged or chemically treated hair a hair restorative composition comprised of:
        an aqueous solvent;
        a hair shaft bonding agent based on at least one of acrylic acid or methacrylic acid for chemically reacting with hair and adhering to and filling in discontinuities in hair shafts within damaged hair in an amount greater than 5% by weight of the hair restorative composition;
        a wetting agent that facilitates absorption of said hair shaft bonding agent into hair shafts being treated; and
        a thickening agent that increases the viscosity of the hair restorative composition before application to damaged hair;
    (b) allowing the hair restorative composition to chemically react with and repair and/or strengthen the damaged or chemically treated hair by adhering to and filling in discontinuities in hair shafts within the damaged or chemically treated hair to yield strengthened and/or repaired hair shafts; and
    (c) washing the hair to remove excess hair restorative composition from the hair, a portion of the hair restorative composition remaining chemically bonded to the hair so as to fill in and permanently mend discontinuities in the strengthened and/or repaired hair shafts after washing.

2. The method as defined in claim 1, wherein said hair shaft bonding agent comprises at least one component selected from the group consisting of acrylic acids, acrylic acid oligomers, acrylic acid polymers, acrylic acid copolymers, acrylates, acrylate oligomers, acrylate polymers, acrylate copolymers, methacrylic acids, methacrylic acid oligomers, methacrylic acid polymers, methacrylic acid copolymers methacrylates, methacrylate oligomers, methacrylate polymers, and methacrylate copolymers.

3. The method as defined in claim 1, wherein said hair shaft bonding agent comprises a mixture of t-butyl acrylate, methacrylic acid, and ethylacrylate copolymer.

4. The method as defined in claim 1, wherein said hair shaft bonding agent is included in a range of about 5.5% to about 30% by weight of said hair restorative composition.

5. The method as defined in claim 1, wherein said wetting agent comprises a silicone polymer.

6. The method as defined in claim 5, wherein said silicone polymer comprises a dimethicone copolymer.

7. The method as defined in claim 1, wherein said wetting agent further acts as a plasticizer or softening agent for said hair restorative composition as it hardens during use.

8. The method as defined in claim 1, said hair restorative composition further comprising a hair conditioner based on at least one protein or amino acid.

9. The method as defined in claim 8, wherein said protein or amino acid comprises hydrolyzed wheat protein.

10. The method as defined in claim 1, wherein said thickening agent comprises at least one cellulosic ether.

11. The method as defined in claim 10, wherein said cellulosic ether comprises hydroxyethyl cellulose.

12. The method as defined in claim 1, wherein said thickening agent comprises at least one of carboxypolymethylene, polyethylene oxide, polyacrylic acid, copolymer of polyacrylic acid, polyacrylate, polyacrylamide, copolymer of polyacrylic acid and polyacrylamide, polyvinylpyrrolidone (PVP), PVP-vinyl acetate copolymer, carboxymethyl-cellulose, hydroxyethyl cellulose sodium acetate, carboxypropylcellulose, polysaccharide gum, or protein.

13. The method as defined in claim 1, said hair restorative composition further comprising at least one pH adjusting agent.

14. The method as defined in claim 13, wherein said pH adjusting agent comprises aminomethyl propanol.

15. The method as defined in claim 1, said hair restorative composition further comprising at least one preservative comprised of at least one of methylparaben and propylparaben, and optionally at least one of propylene glycol or diazolydanyl urea.

16. The method as defined in claim 1, wherein (b) is assisted by drying said hair restorative composition onto the hair using heated air.

17. The method as defined in claim 1, wherein (c) is substantially completed by performing 1 or 2 shampoo washings of the hair.

18. The method as defined in claim 1, further comprising:
    (d) performing a chemical treatment process to the hair comprising at least one of hair straightening, hair perming, body waving, bleaching, coloring, or highlighting.

19. The method as defined in claim 18, the method comprising performing acts (a) through (d) and then repeating acts (a) through (d) at least one time.

20. A method of strengthening damaged or chemically treated hair, comprising:
    (a) applying to damaged or chemically treated hair a hair restorative composition comprised of:
        an aqueous solvent;
        a hair shaft bonding agent for chemically reacting with hair and adhering to and filling in discontinuities in hair shafts within damaged hair in an amount greater than 5% by weight of the hair restorative composition, the hair shaft bonding agent comprising at least one member selected from the group consisting of acrylic acids, acrylic acid oligomers, acrylic acid polymers, acrylic acid copolymers, acrylates, acrylate oligomers, acrylate polymers, acrylate copolymers, methacrylic acids, methacrylic acid oligomers, methacrylic acid polymers, methacrylic acid copolymers methacrylates, methacrylate oligomers, methacrylate polymers, and methacrylate copolymers;
        a wetting agent that facilitates absorption of said hair shaft bonding agent into hair shafts being treated, the wetting agent comprising a silicone polymer; and
        a thickening agent that increases the viscosity of the hair restorative composition before application to damaged hair, the thickening agent comprising at least one member selected from the group consisting of carboxypolymethylene, polyethylene oxides, polyacrylic acids, copolymers of polyacrylic acid, polyacrylates, polyacrylamides, copolymers of polyacrylic acid and polyacrylamide, polyvinylpyrrolidone (PVP), PVP-vinyl acetate copolymers, carboxymethylcellulose, hydroxyethyl cellulose sodium acetate, carboxypropylcellulose, polysaccharide gums, and proteins;

(b) applying heat to the hair and hair restorative composition so as to cause or allow the hair restorative composition to chemically reacting with, adhere to, and fill in discontinuities in hair shafts within the damaged or chemically treated hair to yield strengthened and/or repaired hair shafts; and (c) washing the hair to remove excess hair restorative composition from the hair, a portion of the hair restorative composition remaining chemically bonded to the hair so as to fill in and permanently mend discontinuities in the strengthened and/or repaired hair shafts after washing.

21. The method as defined in claim 20, wherein said wetting agent further acts as a plasticizer or softening agent for said hair restorative composition as it hardens during use.

22. The method as defined in claim 20, said hair restorative composition further comprising a hair conditioner based on at least one protein or amino acid.

23. A method as defined in claim 20, further comprising:

(d) performing a chemical treatment process to the hair comprising at least one of hair straightening, hair perming, body waving, bleaching, coloring, or highlighting.

24. The method as defined in claim 20, wherein said hair shaft bonding agent comprises a mixture of t-butyl acrylate, methacrylic acid, and ethylacrylate copolymer.

25. The method as defined in claim 1, the hair shaft bonding agent repairing damaged hair shafts by adhering back together any loosened cuticle layers, rejoining split ends, and filling in gaps where the cuticle layer has been removed completely.

* * * * *

UNITED STATES PATENT AND TRADEMARK OFFICE
CERTIFICATE OF CORRECTION

PATENT NO. : 7,820,147 B2  
APPLICATION NO. : 11/282892  
DATED : October 26, 2010  
INVENTOR(S) : Mata It is certified that error appears in the above-identified patent and that said Letters Patent is hereby corrected as shown below:

Column 4  
Line 52, change "composition" to --compositions--

Column 5  
Line 23, change "copolymers" to --copolymers,--

Column 6  
Line 18, after "of" insert --restorative composition is not only wasteful but can be uncomfortable and messy,--

Column 7  
Line 20, change "were" to --where--  
Line 55, before "the" insert --after--

Column 8  
Line 59, before "the" insert --of--

Column 9  
Line 24, change "facilitating" to --facilitated--  
Line 66, change "Hydroxyethyel" to --Hydroxyethyl--

Column 10  
Line 12, change "hydroxyethyel" to --hydroxyethyl--

Column 13  
Line 3, change "reacting" to --react--

Signed and Sealed this  
Seventeenth Day of May, 2011

David J. Kappos  
*Director of the United States Patent and Trademark Office*